United States Patent [19]
Akita et al.

[11] Patent Number: 5,545,534
[45] Date of Patent: Aug. 13, 1996

[54] METHOD FOR SCREENING FOR OSTEOPOROSIS

[75] Inventors: Mikio Akita, Kawagoe; Koichi Enomoto, Sayama; Shigeaki Tanaka, Tsurugashima; Yoko Otawara-Hamamoto, Kamifukuoka, all of Japan

[73] Assignee: Hoechst Japan Limited, Tokyo, Japan

[21] Appl. No.: 305,996

[22] Filed: Sep. 19, 1994

[30] Foreign Application Priority Data

Sep. 21, 1993 [JP] Japan ................... 5-234648

[51] Int. Cl.$^6$ .................. G01N 33/53; G01N 33/543
[52] U.S. Cl. .................. 435/4.92; 436/518; 436/804
[58] Field of Search .................... 435/7.92; 436/518, 436/804; 530/350

[56] References Cited

FOREIGN PATENT DOCUMENTS

| A-0557663 | 9/1993 | European Pat. Off. . |
| A-0561297 | 9/1993 | European Pat. Off. . |
| WO91/10141 | 7/1991 | WIPO . |

OTHER PUBLICATIONS

Kinne et al., "Keratan Sulfate Proteoglycan in Rabbit Compact Bone Is Bone Sialoprotien II", J. Biol. Chem., 262(21):10206–10211 (1987).
Somerman et al., "Expression of Attachment Proteins During Cementogenesis", J. Biol. Buccale, 14:207–214 (1990).
Saxne et al, "Increased Release of Bone Sialoprotein Into Synovial Fluid Reflects Tissue Destruction in Rheumatoid Arthritis", Arthritis & Rheumatism, 38(1):82–90 (1995).
Jilka et al., "Increased Osteoclast Development After Estrogen Loss: Mediation by Interleukin–6", Science, 257(5066):88–91 (1992).
Franzen et al., "Isolation and Characterization of Two Sialoproteins Presented Only in Bone Calcified Matrix", Biochem. J., 232:715–724 (1985).
Fisher et al., "Purification and Partial Characterization of Small Proteoglycans I and II, Bone Sialoproteins I and II, and Osteonectin from the Mineral Compartment of Developing Human Bone", J. Biol Chem., 262(20):9702–9708 (1987).
Fisher, L. W. et al., "Matrix Sialoprotein of Developing Bone", J. Biol. Chem., 258(20):12723–12727 (1983).
Ohnishi et al, "Purification, Characterization, and Studies on Biosynthesis of a 59-kDa Bone Sialic Acid–containing Protein (BSP) from Rat Mandible Using a Monoclonal Antibody", J. Biol. Chem., 266(22):14636–14645 (1991).
Chenu, et al., "Platelets Contribute to Circulating Levels of Bone Sialoprotein in Human", J. Bone Miner. Res., 7(1):47–54 (1992).
Fisher et al, J. Biol. Chem., 262(20): 9702–9708 (1987).

*Primary Examiner*—Paula K. Hutzell
*Assistant Examiner*—Patricia A. Duffy
*Attorney, Agent, or Firm*—Finnegan, Henderson, Farabow, Garrett & Dunner, L.L.P.

[57] ABSTRACT

A method for screening for osteoporosis comprising bone sialoprotein of mammals. Osteoporosis can be screened by bringing the body fluid sample collected from a living body into contact with the above-mentioned diagnostic agent to immunochemically detect the antibody which is present in the said sample and specifically reacts with the said diagnostic agent.

4 Claims, 1 Drawing Sheet

METHOD FOR SCREENING FOR OSTEOPOROSIS

BACKGROUND OF THE INVENTION

1. Field of the Invention

This invention relates to a diagnostic agent for osteoporosis which comprises a mammalian bone sialoprotein and a method for diagnosis of osteoporosis using the same. More particularly, this invention is concerned with a new immunochemical diagnostic agent and a new method for diagnosis, which can make pathogenetic classification of osteoporosis feasibility. Moreover, there may be suggested a different therapy from the prior ones, e.g., utilization of an immunosuppressing agent, to osteoporotic patients classified according to the present method.

2. Description of the Prior Art

Degenerative osteoporosis is a syndrome showing a reduced amount of bone owing to unknown causes with aging after growth period and subsequent clinical pictures such as easy fractures of bones, lumbago and dorsalgia and the like. As the diagnostic methods for osteoporosis presently applied, there may be mentioned X-ray photographing of bones (MD method), DPA (Dual Photon Absorptiometry), DEXA (Dual Energy X-ray Absorptiometry), CXD (Computed X-ray Densitometry) and determination of a bone mineral amount, a bone density and the like by means of a physical apparatus for determining a bone amount using a low-frequency ultrasonic wave and the like. To determine a bone amount of an individual at a certain age according to such diagnostic methods makes it feasible to judge a person of his or her any future possibility of fractures. More specifically, a remarkable reduction in bone density could suggest a high risk of fractures in the future.

It has been considered, however, that a reduced bone density is only one of dangerous factors for possible fractures and a fracture risk would be also increased owing to phenomena with aging such as a lowered elasticity of collagen fibers, qualitative deterioration of the bone structure, lowered muscular power and so on. These dangerous factors other than lowered muscular power could not presently be determined noninvasively, which remains as an important problem to be solved in the future.

On the other hand, a noninvasive method for determining a bone density, which is a main diagnostic method for osteoporosis, and an invasive method for determining a bone form by biopsy have recently been developed remarkably. However, each of these methods alone may not satisfy all the clinical requirements, so that the most preferred determination method may be selected in compliance with the purpose and any optional combination therewith may be attempted under the present conditions.

The maximum bone density for an individual is attained at ages of 30–40, which is referred to as the peak bone mass. A risk for fractures should be evaluated upon the duration and the rate wherein the peak bone mass could be reduced, but it is impossible to determine bone density retroactively and one should evaluate upon an absolute value when determined. Accordingly, any qualitative changes in bone when a bone density is to be determined or in the very near past could not be determined by the prior non-invasive determination method.

In order to supplement such drawbacks in the current bone density determination methods, attempts have been made to understand pathosis by determining a blood concentration or a urinary excretion level of a bone metabolism controlling factor (parathyroid hormone; PTH), an activated vitamin (1, 25$(OH)_2D_3$), calcitonin and the like), or various factors liberated from bone tissues with bone metabolic remodeling (alkaline phosphatase, acid phosphatase, pyridinoline, deoxypyridinoline, type-1 procollagen peptide, osteocalcin and the like), but there remain many points unsatisfied.

As regressive osteoporosis is a syndrome which is defined to be a reduced bone amount due to unknown causes, a pathogenetic diagnosis has not been attempted. In other words, the secondary osteoporosis with identified pathogenesis has hitherto been excluded from regressive osteoporosis. This invention is directed to an epoch-making diagnostic method which can classify a part of osteoporosis due to unknown causes as one of autoimmune diseases.

Detailed Description of the Invention

Osteoporosis has been frequently developed in women as many autoimmune diseases do and also observed in the elder age with many immunological abnormalities. Moreover, it was reported that in rheumatoid arthritis, a noticeable reduction in bone amount be developed in bones near the cavitas articulare through which a large amount of cytokine such as IL-1 and others is liberated. On the other hand, it was elucidated by Manolagas et al. that the cytokine, which plays a role in differentiation and induction of osteoclast, the leading role for bone adsorption, be IL-6 and IL-11 (Jilka et al., Science, vol. 257, p. 88–91 , 1992).

On the other hand, it is also well-known that the osteoclast is the cell having the same origin as such immunocompetent cells as monocytes or macrophages. As shown above, it has now been elucidated that the cytokine which has been considered to have no direct relation to bone functions has, in fact, closely related to bone metabolism.

These facts may suggest a possibility of any immunoabnormality taking part in the onset of osteoporosis. Further, the presence of the bone marrow within bone may suggest an important influence of the blood immunocytes produced in bone marrow upon bone metabolic remodeling.

Then, the present inventors have attempted to investigate an antibody of the bone matrix protein specifically found in the serum from osteoporotic patients to find that an antibody to the antigen of bone sialoprotein (BSP) is present in the patient serum by means of an enzymeimmunoassay (ELISA). Although the BSP antibody could not be found at all in the serum from normal persons, the antibody could be detected at a high frequency in the group of patients suffering from osteoporosis. The BSP is involved in human bones in a relatively large amount, but such an autoantibody to BSP has not been reported up to now. Thus, a novel and simplified differential diagnostic agent and a diagnostic method for osteoporosis according to this invention have been now completed.

Upon the fact that the BSP antibody is found in the serum from osteoporotic patients, there has been suggested the possibility that autoimmune reaction would closely participate in the onset of osteoporosis and the development of its clinical picture. Accordingly, there is greatly expected the development of a novel therapy using an immunosuppressive agent and the like, in addition to the prior therapy for osteoporosis.

Although the development mechanism of the autoantibody to BSP has not fully been elucidated, it would be of no doubt that abnormality of immunity should be behind. It may also be supposed that the BSP antibody as developed could cause any qualitative changes in the bone matrix, which may also be of a microenvironment for bone, leading to deterioration of the clinical picture and possibly deterioration of osteogenesis by osteoblast.

In general, a therapy for osteoporosis when a bone density has been lowered is less effective and it would be desirable to make diagnosis before the condition of disease progresses, so that there may be considered as requisite a so-called mass-screening on healthy persons. From this point of view, a diagnostic method for osteoporosis with superior safety, simplicity and economization as characterized in this invention could be very important.

The bone sialoprotein (BSP) as used in this invention was known to be found in mammalian bones. In particular, the bovine BSP was elucidated to be a protein containing a large amount of sialic acid and having a molecular weight of 25 Kd by its first purification from bovine bones and investigation on its properties made by Herring et al. in the middle of 1960's (Herring, G. M., The Biochemistry and Physiology of Bone, vol. I, U.S.A., Academic Press, 1972). However, it has been recently elucidated that the 25 Kd-MW protein was a degradation product of the BSP having a molecular weight of 57 Kd (Franzen, A. et al, Biochem, J., vol. 232,p. 715–724, 1985). Further, it has been known that BSP is one of the main noncollagenous proteins found in bone tissues (Larry, W. F. et al., J. Biol. Chem., vol. 262, p. 9702–9708, 1987).

The said protein is found specifically in such mineralized tissues as bones or teeth (Fisher, L. W. et al., J. Biol. Chem., vol. 258, p. 12723–12727, 1983) and it is widely found in bones by synthesis on osteoblasts and osteocytes (Ohnishi et al., J. Biol. Chem., vol. 266, p. 14636–14645, 1991). Biological functions and others of BSP, however, have not yet been elucidated and are left as the subjects to be studied hereafter.

Also, on the 13-amino acids sequence at the N-terminus region of the said protein, 70% homology was observed between the human and bovine ones (Chenu, C. et al., J. Bone Miner, Res., vol. 7, p. 47–54, 1992). The high homology of the amino acid sequence indicates that BSP could be well conserved among the species and the BSP derived from non-human mammals such as bovine could be also applied to differential diagnosis of patients suffering from osteoporosis.

As discussed above, this invention is directed to a diagnostic agent for human osteoporosis which comprises an antigen capable of reacting with an antibody of the serum from osteoporotic patients but not reacting with an antibody of the normal human serum, the antigen being present in animal bone tissues and to a diagnostic method using the same.

As examples of this assay, using the BSP extracted from the bone of mammals such as bovine, which may be purified with an ion exchange chromatography and the like as the present diagnostic agent, there may be mentioned (1) the ELISA technique wherein the purified antigens are fixed onto a 96-well plastic microplate, a human serum is added as a test sample to proceed with the reaction and then an enzyme-labelled secondary antibodies are allowed to react and an enzymatic color developed by the enzyme is detected by a detector, (2) the RIA technique wherein the present diagnostic agent is fixed into a plastic tube, a human serum is allowed to react, radio isotope-labelled secondary antibodies are allowed to react instead of the enzyme-labelled secondary antibodies and an amount of the isotope bound is detected by a detector, (3) the Western blotting technique wherein the proteins in the bone extract containing the present diagnostic agent are separated according to their molecular weights by electrophoresis using SDS polyacrylamide gel containing a reducing agent, the protein is transferred from the gel onto a nitrocellulose membrane, the membrane is allowed to react with a serum test sample, secondary antibodies labelled with an enzyme or isotope is further allowed to react and then the reaction is visually discriminated, and the like.

These assay techniques are all well-known to those skilled in the art and, as an exemplary report to be referred to, general immunochemical assays including the ELISA technique, Western blotting technique and others are explained in detail in "Immunological Methods I, II" (Lefkovits & Pernis, U.S.A., Academic Press, 1979, 1981), "Methods in Enzymology", vol. 70, 73, 74 and 84 (Langone & Van Vunakis, U.S.A., Academic Press, 1980, 1981, 1982) and the like.

As the results by enzyme immunoassay, the absorbance (OD) beyond the mean value of the sera obtained from 45 normal persons +3SD (standard deviation) was observed in about 20% of 123 cases of the sera from osteoporotic patients. As is shown, an antibody to the bone matrix proteins (bone sialoproteins/BSP) was detected in osteoporosis state, but such a finding has not yet been reported in autoimmune diseases and should be characteristic of osteoporosis.

This invention will be more illustratively explained by way of the following Examples.

EXAMPLE 1

Preparation of Diagnostic Agent
Extraction of bone sialoprotein from bovine bone tissues
(1) Material and Extraction
Defatted and ground bovine bones were treated with 4M guanidine-hydrochloride, 50 mM acetate buffer (containing a protease inhibitor) at pH 5.8 at 4° C. for 24 hours and then centrifuged. The residue thus obtained was further treated at 4° C. for 48 hours using 4M guanidine hydrochloride, 250 mM EDTA, 50 mM Tris-hydrochloride buffer (pH 7.4) to extract BSP. The supernatant obtained by centrifugation was concentrated and then used for purification of BSP (guanidine hydrochloride/EDTA extract).
(2) Purification
i) DEAE Ion Exchange Column Chromatography (pH 6.0)
The guanidine-hydrochloride/EDTA extract was replaced with 6M urea, 10 mM Tris, 0.1M acetate buffer (pH 6.0) and then fractionated by means of DEAE-Toyopearl column (Tosoh Corp.).

The protein adsorbed on the column was eluted with acetic acid at a concentration gradient of 0.1M to 1.2M. Each fraction of the column eluates was determined for protein mass (absorption wavelength 280 nm) and sialic acid content (periodic acid-resorcinol reaction) to select those fractions having a higher content of sialic acid as BSP fraction.
ii) DEAE Ion Exchange Column Chromatography (pH 4.0)
The BSP fraction obtained in the above i) was replaced with 6M urea, 10 mM Tris, 10 mM sodium chloride, 50 mM acetate buffer (pH 4.0) and then refractionated with DEAE-Toyopearl column (Tosoh Corp.). The protein was eluted with sodium chloride at a concentration gradient of 50 mM to 500 mM. Each fraction was determined for its protein mass and sialic acid content to select those fractions having a higher content of sialic acid as BSP fraction.

iii) Reversed Phase Column Chromatography

The BSP fraction obtained in the above ii) was further purified using a reversed phase column (C-18, VYDAC Separation Groups Corp.) at a $CH_3CN$ concentration gradient of 0–100%. Also, electrophoresis was carried out using SDS polyacrylamide gel to confirm its molecular weight and purity.

iv) Gel Filtration

The BSP fraction obtained in the above iii) was freeze-dried, dissolved in 6M urea, 0.5M sodium chloride, 10 mM Tris-hydrochloride buffer (pH 7.2) and further purified by gel filtration with Superose 12 perp 60/600 (Pharmacia) column. The molecular weight and purity of the purified fraction were confirmed by electrophoresis using SDS polyacrylamide gel.

(3) Confirmation by amino acid analysis

Amino acid analysis was carried out for the BSP fraction obtained after the gel filtration (PICO-TAG amino acid analyzer, Waters Inc., U.S.A.). The purified BSP showed an extremely similar amino acid composition to that of the previously reported BSP.

EXAMPLE 2

Detection of autoantibody to bone sialoprotein using enzyme immunoassay

The BSP (1 mg/ml) obtained in Example 1 was diluted 200 times (50 µg/ml) with a phosphate-buffered saline, and pipetted into the holes of a 96-well microplate at 50 µl/well and allowed to stand at 4° C. overnight (coating procedure).

Thereafter, the microplate coated with the said protein was washed three times with a phosphate-buffered saline containing 0.05% Tween 20 and Tris-buffered saline (pH 7.4) containing 0.5% casein was pipetted into each well at 250 µl (Blocking procedure) and allowed to stand at room temperature for one hour. Then, the plate was further washed three times and 50 µl each of the sera of patients suffering from osteoporosis and of normal persons, which were diluted 200 times with Tris-buffered saline containing 0.5% casein, was pipetted into each well and reaction was allowed to proceed for 3 hours by shaking at room temperature (Primary reaction).

After completion of the primary reaction, the plate was again washed three times with a phosphate-buffered saline containing 0.05% Tween 20 and then the anti-human IgG-peroxidase-labelled antibody, which was diluted 4000 times with Tris-buffered saline containing 0.5% casein, was pipetted into each well at 50 µl. Reaction was then allowed to proceed at room temperature for 2 hours (Secondary reaction).

After completion of the secondary reaction, the plate was again washed three times, substrate solution/color former (chromogen substrate) were pipetted into each well at 50 µl and reaction was allowed to proceed at room temperature for 30 minutes.

After the reaction was continued for 30 minutes, the reaction was discontinued with 0.5N dilute sulfuric acid and measurement was carried out using a colorimeter (BEP-II, Behringwerke AG, Germany) with a dominant wavelength of 450 nm and a complementary wavelength of 650 nm. The results are shown in FIG. 1. In normal human sera, all measurements except for the two boundary cases were within the range of a mean value plus 3SD (standard deviation), whereas a higher absorbance value beyond the said range was observed in 25 cases of 123 cases of the sera of patients suffering from osteoporosis.

EXAMPLE 3

Detection of autoantibody to bone sialo protein according to Western blotting technique To 50 µl of the bone sialoprotein obtained in Example 1 (concentration of 1 mg/ml) was added 50 µl of 2 ME-containing Tris-SDS sample treating solution and, after stirring thoroughly, reduction with heating was carried out at 80° C. for 10 minutes. The sample thus treated was placed onto a SDS-PAGE plate (available from Daiichi Kagaku Yakuhin K.K.) with a gel concentration gradient of 4–20% at an amount of 5 µg/cm of gel and electrophoresis was carried out at a constant current of 30 mA. At the point when the migration end of the electrophoresis approached the end of the gel by about 5 mm, the power supply was turned off, a nitrocellulose membrane was placed on the gel and transfer was made at 40 V in a refrigeration chamber at 8° C. overnight. After completion of the transfer, from the end of the membrane was cut off a portion with a length of 2–3 cm and protein staining was done with Coomassie Brilliant Blue to confirm transfer of the said protein onto the membrane. The membrane was dipped into Tris-buffered saline containing 0.5% casein and blocking was carried out at 4° C. overnight. The membrane in which blocking was completed was cut into strips, each having a width of 4–5 mm, which were then immersed in the sera of patients and normal persons diluted 400 times with the casein-containing Tris-buffered saline used for the blocking procedure and the primary reaction was allowed to proceed for 4 hours while shaking at room temperature. After completion of the primary reaction, the membrane was washed well with a phosphate-buffered saline containing 0.05% Tween 20.

Thereafter, the membrane was immersed in anti-human IgG-biotin-labelled antibody (rabbit) diluted 3000 times with a Tris-buffered saline containing 0.5% casein and the reaction was effected at room temperature while shaking.

Then, the membrane was immersed in a peroxidase-conjugated streptavidin diluted 500 times with a Tris-buffered saline containing 0.5% casein and the tertiary reaction was carried out at room temperature for 2 hours while shaking. After completion of the reaction, washing was carried out on the same manner as done after completion of the primary reaction. The membrane after completion of the washing was colored by addition of a color former [a methanolic solution of 4-chloro-1-naphthol (6 mg/ml)/30% hydrogen peroxide. As a result, the band for the molecular weight of about 58 Kd was detected which is specific to osteoporotic patients.

Figure 1:
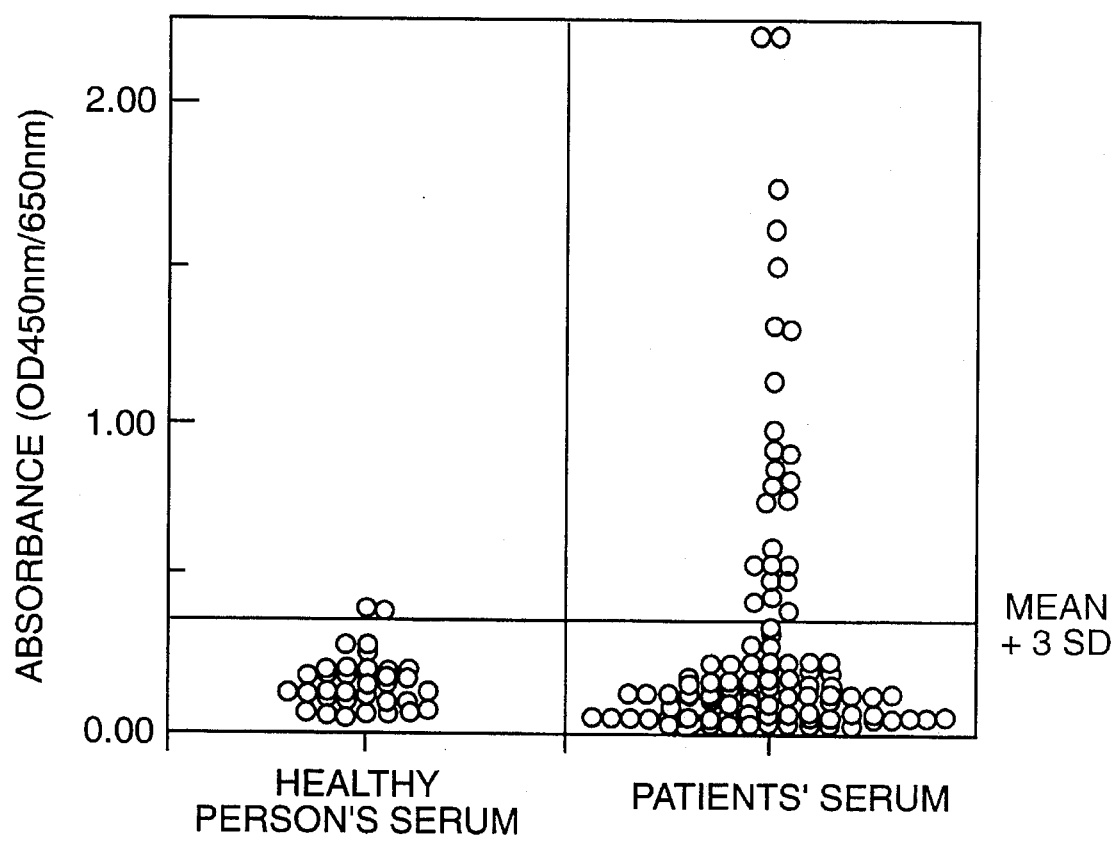
FIG. 1 is a graph showing absorbance on the serum from healthy persons and that from patients suffering from osteoporosis obtained in Example 2.

What is claimed is:

1. A method for screening for osteoporosis which comprises the steps of:

(1) bringing a body fluid sample collected from a living body into contact with a diagnostic agent which comprises a mammalian bone sialoprotein; and (2) detecting the amount of antibody which specifically binds to said diagnostic agent.

2. The method for screening as claimed in claim 1 wherein said antibody is detected by ELISA.

3. The method for screening as claimed in claim 1 wherein said antibody is detected by RIA.

4. The method for screening as claimed in claim 1 wherein said antibody is detected by Western blotting technique.

* * * * *